(12) United States Patent
Schafran et al.

(10) Patent No.: US 8,772,004 B2
(45) Date of Patent: Jul. 8, 2014

(54) SYSTEM AND METHOD FOR HIGH-VOLTAGE PULSE ASSISTED AGGREGATION OF ALGAE

(75) Inventors: Gary C. Schafran, Norfolk, VA (US); Juergen F. Kolb, Norfolk, VA (US); Aron Stubbins, Savannah, GA (US); Karl H. Schoenbach, Norfolk, VA (US)

(73) Assignee: Old Dominion University Research Foundation, Norfolk, VA (US)

( * ) Notice: Subject to any disclaimer, the term of this patent is extended or adjusted under 35 U.S.C. 154(b) by 199 days.

(21) Appl. No.: 12/823,696

(22) Filed: Jun. 25, 2010

(65) Prior Publication Data
US 2011/0003350 A1  Jan. 6, 2011

Related U.S. Application Data

(60) Provisional application No. 61/220,417, filed on Jun. 25, 2009.

(51) Int. Cl.
*C12N 13/00* (2006.01)

(52) U.S. Cl.
USPC .......... 435/173.9; 435/173.1; 435/257.1; 435/261; 210/702; 210/703; 210/719; 210/721; 210/748.01; 210/767

(58) Field of Classification Search
None
See application file for complete search history.

(56) References Cited

U.S. PATENT DOCUMENTS

| | | |
|---|---|---|
| 2,171,490 A | 8/1939 | Dalpayrat |
| 4,055,491 A | 10/1977 | Porath-Furedi |
| 4,107,026 A | 8/1978 | Freeman |
| 4,168,222 A | 9/1979 | Freeman |
| 4,170,529 A | 10/1979 | Freeman |
| 4,207,158 A | 6/1980 | Freeman |
| 4,236,349 A | 12/1980 | Ramus |
| 4,292,408 A * | 9/1981 | Zimmermann et al. ... 435/173.6 |
| 4,561,953 A | 12/1985 | Muralidhara et al. |
| 4,802,964 A | 2/1989 | Muralidhara et al. |
| 4,861,496 A | 8/1989 | Diaz |
| 4,971,705 A | 11/1990 | Roslonski |
| 4,983,189 A | 1/1991 | Peterson et al. |
| 5,019,230 A | 5/1991 | Candor |
| 5,020,977 A | 6/1991 | Lucas |
| 5,043,048 A | 8/1991 | Muralidhara |
| 5,049,248 A | 9/1991 | Muralidhara et al. |
| 5,064,515 A | 11/1991 | Harapanahalli |
| 5,075,012 A | 12/1991 | Busse |
| 5,098,538 A | 3/1992 | Kim et al. |
| 5,230,809 A | 7/1993 | Roslonski |
| 5,259,940 A | 11/1993 | Candor |
| 5,292,421 A | 3/1994 | Senapati et al. |
| 5,326,530 A | 7/1994 | Bridges |
| 5,344,533 A | 9/1994 | Candor |
| 5,344,535 A | 9/1994 | Betts |
| 5,362,371 A | 11/1994 | Candor |
| 5,403,455 A | 4/1995 | Candor |
| 5,435,893 A | 7/1995 | Sun et al. |
| H001568 H | 8/1996 | Huang et al. |
| 5,593,565 A | 1/1997 | Ajdari |
| 5,653,859 A | 8/1997 | Parton et al. |
| 5,695,650 A | 12/1997 | Held |
| 5,711,888 A | 1/1998 | Trampler et al. |
| 5,891,342 A | 4/1999 | Tije |
| 5,893,979 A | 4/1999 | Held |
| 6,030,538 A | 2/2000 | Held |
| 6,325,916 B1 | 12/2001 | Lambert et al. |
| 6,326,177 B1 | 12/2001 | Schoenbach et al. |
| 6,524,486 B2 | 2/2003 | Borodyanski et al. |
| 6,871,744 B2 | 3/2005 | Miller et al. |
| 6,881,314 B1 | 4/2005 | Wang et al. |
| 7,001,520 B2 | 2/2006 | Held et al. |
| 7,340,957 B2 | 3/2008 | Kaduchak et al. |
| 7,347,923 B2 | 3/2008 | Cummings et al. |
| 7,462,287 B2 | 12/2008 | Berrak et al. |
| 7,507,341 B2 | 3/2009 | Gallagher |
| 7,572,369 B2 | 8/2009 | Gallagher et al. |
| 7,572,623 B2 | 8/2009 | Mangano |
| 7,578,918 B2 | 8/2009 | Berrak et al. |

(Continued)

FOREIGN PATENT DOCUMENTS

| | | |
|---|---|---|
| WO | WO-97/07065 A1 | 2/1997 |
| WO | WO-2007/114528 A1 | 10/2007 |

(Continued)

OTHER PUBLICATIONS

Alfafara, CG et al. Operating and scale-up factors for the electrolytic removal of algae from eutrophied lakewater. Journal of Chemical Technology and Biotechnology. 2002. 77: 871-876.*
Khosla, NK et al. Pulsed electrogeneration of bubbles for electroflotation. Journal of Applied Electrochemistry. 1991. 21: 986-990.*
Poelman, E. et al. Potential of electrolytic flocculation for recovery of micro-algae. Resources, Conservation and Recycling. 1997. 19: 1-10.*
Miao, X et al. Biodiesel production from heterotrophic microalgal oil. Bioresources Technology. 2006. 97: 841-846.*
"Chapter 2: Generation of Plasma in Liquid." in: Yang, Y. et al., Plasma Discharge in Liquid (New York, CRC Press, 2012), pp. 15-31. [online]. [retrieved on Nov. 14, 2012]. Retrieved from the Internet: <URL:http://www.crcnetbase.com/doi/abs/10.1201/b11650-3>.*
Shimizu, N et al. A novel method of hydrogen generation by water electrolysis using an ultra-short-pulse power supply. Journal of Applied Electrochemistry. 2006. 36: 419-423.*

(Continued)

*Primary Examiner* — Allison Ford
*Assistant Examiner* — Susan E Fernandez
(74) *Attorney, Agent, or Firm* — Len Smith, Esq.; Justin Kniep, Esq.; Wilmer Cutler Pickering Hale and Dorr LLP

(57) ABSTRACT

A method and device for aggregating algae in an aqueous solution is disclosed. The method can include providing an algae feed comprising a liquid and algae dispersed therein. The algae feed can be aggregated by applying a nanosecond pulsed electric field to the algae feed. The nanosecond pulsed electric field can include a plurality of electric pulses having a pulse duration ranging from 1 to 1,000 nanoseconds. The method can also include separating an aggregated algae stream from the algae feed and feeding the aggregated algae stream to a lipid extraction operation.

10 Claims, 1 Drawing Sheet

(56) References Cited

U.S. PATENT DOCUMENTS

| | | | |
|---|---|---|---|
| 7,645,382 | B2 | 1/2010 | Gallagher et al. |
| 7,695,621 | B2 | 4/2010 | Gallagher et al. |
| 7,730,558 | B2 | 6/2010 | Choe |
| 7,828,953 | B2 | 11/2010 | Berrak et al. |
| 7,837,040 | B2 | 11/2010 | Ward et al. |
| 7,931,784 | B2 | 4/2011 | Medoff |
| 7,943,031 | B2 | 5/2011 | Jones et al. |
| 7,950,181 | B2 | 5/2011 | Mccall |
| 7,998,225 | B2 | 8/2011 | Powell |
| 8,083,068 | B2 | 12/2011 | Kaduchak et al. |
| 8,227,257 | B2 | 7/2012 | Ward et al. |
| 8,425,749 | B1 | 4/2013 | Ravula |
| 2003/0150789 | A1 | 8/2003 | Miller et al. |
| 2003/0159932 | A1 | 8/2003 | Betts et al. |
| 2004/0079650 | A1 | 4/2004 | Morkovsky et al. |
| 2005/0016870 | A1 | 1/2005 | Berrak et al. |
| 2005/0199499 | A1 | 9/2005 | Berrak et al. |
| 2006/0269531 | A1 | 11/2006 | Beebe et al. |
| 2007/0048859 | A1 | 3/2007 | Sears |
| 2007/0227904 | A1 | 10/2007 | Miller et al. |
| 2008/0044891 | A1 | 2/2008 | Kinley et al. |
| 2009/0090673 | A1 | 4/2009 | Jensen et al. |
| 2009/0181438 | A1 | 7/2009 | Sayre |
| 2009/0206171 | A1 | 8/2009 | Friend et al. |
| 2010/0078384 | A1 | 4/2010 | Yang |
| 2010/0078389 | A1 | 4/2010 | Elektorowicz et al. |
| 2010/0116686 | A1 | 5/2010 | Wiemers et al. |
| 2010/0129559 | A1 | 5/2010 | Dermoune et al. |
| 2010/0163428 | A1 | 7/2010 | Dermoune et al. |
| 2010/0233761 | A1 | 9/2010 | Czartoski |
| 2010/0236931 | A1 | 9/2010 | Fernando |
| 2010/0261918 | A1 | 10/2010 | Chianelli et al. |
| 2010/0314323 | A1 | 12/2010 | Lean et al. |
| 2011/0086386 | A1 | 4/2011 | Czartoski et al. |
| 2011/0095225 | A1 | 4/2011 | Eckelberry et al. |
| 2011/0123392 | A1 | 5/2011 | Dionne et al. |
| 2011/0127164 | A1 | 6/2011 | Sinha et al. |
| 2011/0262990 | A1 | 10/2011 | Wang et al. |
| 2012/0040428 | A1 | 2/2012 | Reep et al. |
| 2012/0055797 | A1 | 3/2012 | Dermoune et al. |
| 2012/0091000 | A1 | 4/2012 | Taylor et al. |
| 2012/0095245 | A1 | 4/2012 | Lane et al. |
| 2012/0129244 | A1 | 5/2012 | Green et al. |
| 2012/0193297 | A1 | 8/2012 | Lean |
| 2012/0205257 | A1 | 8/2012 | Collier |
| 2012/0295338 | A1 | 11/2012 | Reep et al. |
| 2012/0325727 | A1 | 12/2012 | Dionne et al. |
| 2012/0328477 | A1 | 12/2012 | Dionne et al. |
| 2012/0329121 | A1 | 12/2012 | Green et al. |
| 2012/0329122 | A1 | 12/2012 | Lipkens et al. |
| 2013/0061518 | A1 | 3/2013 | Schafran et al. |
| 2013/0079236 | A1 | 3/2013 | Holmes |
| 2013/0116459 | A1 | 5/2013 | Marrone et al. |
| 2013/0137154 | A1 | 5/2013 | Reep |
| 2013/0164798 | A1 | 6/2013 | Vanhercke et al. |
| 2013/0164812 | A1 | 6/2013 | Nicholas et al. |
| 2013/0192130 | A1 | 8/2013 | Eckelberry |
| 2013/0211113 | A1 | 8/2013 | Eckelberry |
| 2013/0228464 | A1 | 9/2013 | Eckelberry |
| 2013/0288329 | A1 | 10/2013 | Sanchez |
| 2014/0017754 | A1 | 1/2014 | Kale |
| 2014/0017755 | A1 | 1/2014 | Kniep |
| 2014/0017756 | A1 | 1/2014 | Kniep |
| 2014/0017757 | A1 | 1/2014 | Kniep |
| 2014/0017758 | A1 | 1/2014 | Kniep |
| 2014/0017759 | A1 | 1/2014 | Kniep |
| 2014/0017760 | A1 | 1/2014 | Kniep |

FOREIGN PATENT DOCUMENTS

| | | |
|---|---|---|
| WO | WO-2010/067340 A1 | 6/2010 |
| WO | WO-2011/000079 A1 | 1/2011 |
| WO | WO-2011/054081 A1 | 5/2011 |
| WO | WO-2011/063512 A1 | 6/2011 |
| WO | WO-2012/000056 A1 | 1/2012 |
| WO | WO-2012/054404 A2 | 4/2012 |
| WO | 2013055819 | 4/2013 |
| WO | 2013116357 | 8/2013 |
| WO | 2013158795 | 10/2013 |

OTHER PUBLICATIONS

Schultheiss et al., Processing of Sugar Beets with Pulsed-Electric Fields, IEEE Trans. Plasma Sci., 30: 1547-1551 (2002).

Li et al., The Effects of Pulsed Streamerlike Discharge on Cyanobacteria Cells, IEEE Trans. Plasma Sci., 34: 1719-1724 (2006).

Anna Austin, A Shocking Ethanol Enhancer, Ethanol Producer Magazine (Mar. 2009), available at http://www.ethanolproducer.com/article-print.jsp?article_id=5344, last visited Apr. 7, 2009, 3 pages.

Sommerfeld et al., Application of Electroporation for Lipid Extraction from Microalgae, ASU, no date available, 1 page.

Sina Salim, Biofuels from Microalgae. Harvesting of Algae for Oil Extraction, Thesis, Wageningen University (no date given), available at http://www.bpe.wur.nl/wever.internet/Print.Vrije_Content_Contat.asp . . . , lasted visited May 20, 2009, 2 pages.

Friedrich, U. et al., "High Efficiency electrotransfection with aluminum electrodes using microsecond controlled pulses," Bioelectrol. Bioenerg., vol. 47: 103-111 (1998).

Mankowski, J. and Kristiansen, M. "A Review of Short Pulse Generator Technology," IEEE Translations on Plasma Science, 28(1): 102-108 (2000).

Author Unknown, "Actoustic Algae? Solix & Los Alamos Lab Team Up," Cleantech News and Analysis, retrieved from http://gigaom.com/cleantech/acoustic-algae-solix-los-alamos-lat-team-up on Jul. 23, 2012, 9 pages.

Author Unknown, Cotwell Industries, Inc., "Telescoping Tubing," retrieved from http://www.coltwell.com/telescoping_tubing.html. On Oct. 1, 2012, 1 page.

Azarian et al., "Algae Removal by Electro-coagulation Process, Application for Treatment of the Effluent from an Industrial Wastewater Treatment Plant," Iranian J. Publ. Health, vol. 36, No. 4, 2007, pp. 57-64, downloaded from http://journals.tums.ac.ir on Apr. 13, 2012.

Bosma, et al., "Ultrasound, a new separation technique to harvest microalgae," Journal of Applied Phycology 15, 2003, pp. 143-153.

Brennan, et al., "Biofuels from Microalgae—A Review of Technologies for Production, Processing, and Extractions of Biofuels and Co-products," Renewable and Sustainable Energy Reviews, 14, 2010, pp. 557-577.

Gao et al., "Electro-coagulation-flotation Process for Algae Removal," Journal of Hazardous Materials 177, 2010, pp. 336-343.

Kim et al., "Continuous Microalgae Recovery Using Electrolysis with Polarity Exchange," Bioresource Technology, 111, 2012, pp. 268-275.

Loveless, "Utilizing Standing Ultrasonic Waves to Harvest Microalgae from a Fluid Suspension," a Senior Scholars Thesis, Submitted to the Office of Undergraduate Research, Texas A&M University for partial fulfillment of the requirements for the designation as Undergraduate Research Scholar, Apr. 2010, 38 pages.

Mide Volture, "Piezoelectric Energy Harvesters," Revision Date Jun. 2010, retrieved from http:/www.mide.com/pdfs/Volture_Datasheet_001 on Aug. 1, 2012, 24 pages.

OriginOil Company Presentation, "Converting Algae to Renewable Crude Oil," Rev Mar. 2012, OTC/BB: Ooil, www.originoil.com, 35 pages, Accessed Apr. 11, 2012.

OriginOil, "Algae Appliance," 2011, retrieved from http://www.originoil.com/pdf.Algae-Applance-Product-Data-Sheet on Nov. 29, 2011, 2 pages.

Schwartz, "Algae Industry Magazine," AIM Interview: LANL's Jose Olivares: Algae Industry Magazine, retrieved from http://www.algaeindustrymagazine.com/aim-interview-lanls-jose-olivares on Jul. 23, 2012, 13 pages.

Sherrit, "The physical Acoustiics of Energy Harvesting," IEEE International Ultrasonics Symposium Proceedings, 2008, pp. 1046-1055.

(56) References Cited

OTHER PUBLICATIONS

Sousa, "Gridless Tube from 1938," Radiomuseum, retrieved from http://www.radiomuseum.org/forum/gridless_tube.html on Oct. 1, 2012, 7 pages.

Uduman et al., "A Parametric Study of Electrocoagulation as a Recovery Process of Marine Microalgae for Biodiesel Production," Chemical Engineering Journal 174, 2011, pp. 249-257.

Uduman et al., "Electrocoagullation of Marine Microalgae," Chemeca 2011: Engineering a Better World, Sydney Hilton Hotel, NSW, Australia, 18-21 Sep. 2011, Barton, A.C.T., Engineers Australia, 2011, 11 pages.

Uduman, N. et al. "Dewatering of microalgal cultures: A major bottleneck to algae-based fuels," Journal of Renewable and Sustainable Energy 2, 2010, 012701-1-012701-15.

Vandamme et al., "Evaluation of Electro-Coagulation-Flocculation for Harvesting Marine and Freshwater Microalgae," Biotechnology and Bioengineering, vol. 108, No. 10, Oct. 2011, pp. 2320-2329.

Xu et al., "Development of an Efficient Electroflocculation Technology Integrated with Dispersed-Air Flotation for Harvesting Microalgae," J. Chem. Technol. Botechnol. 2010, 85, pp. 1504-1507.

Dufreche et al., "Extraction of Lipids from Municipal Wastewater Plant Microorganisms for Production of Biodiesel," J. Amer. Oil Chem. Soc., 2007, 84, pp. 181-187.

Communication Relating to the Results of the Partial International Search for International Application No. PCT/US2013/050064 as performed by the International Searching Authority, the European Patent Office, mailing date Feb. 3, 2014, 2 pages.

\* cited by examiner

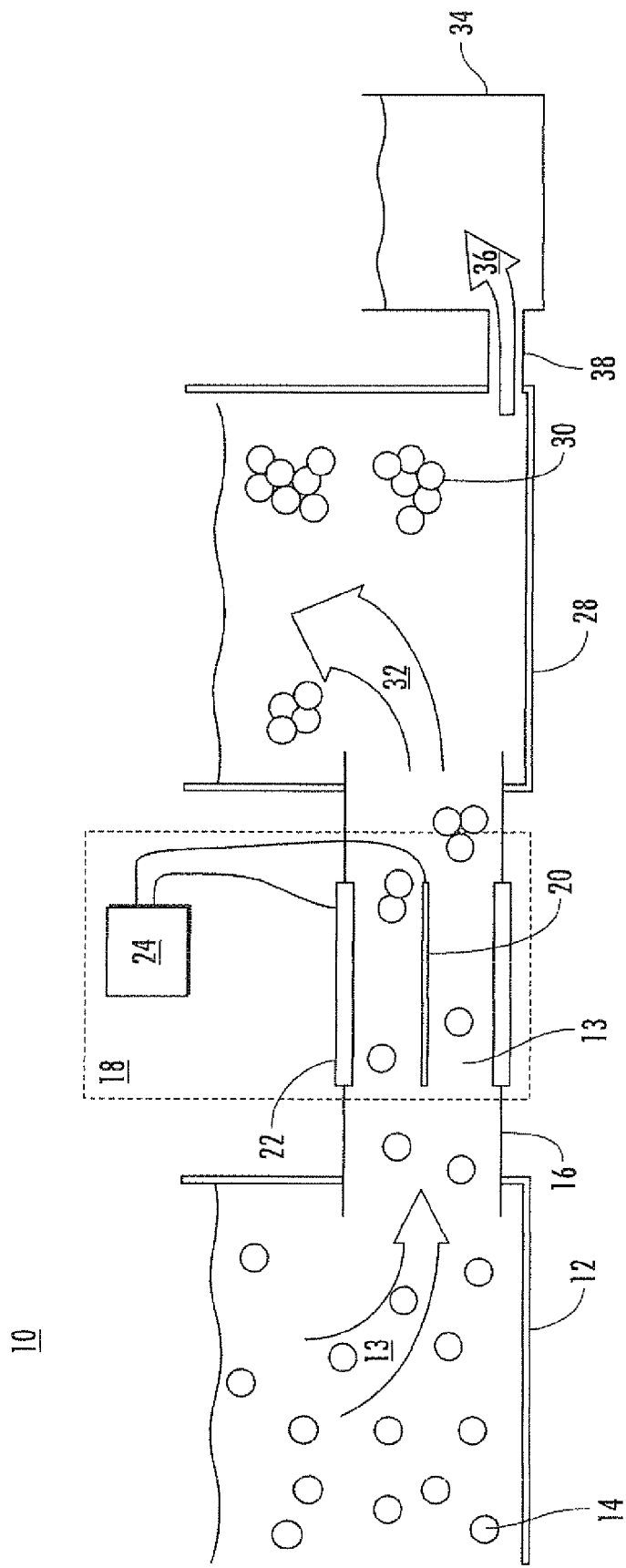

SYSTEM AND METHOD FOR HIGH-VOLTAGE PULSE ASSISTED AGGREGATION OF ALGAE

CROSS REFERENCE TO RELATED APPLICATIONS

This application claims priority to U.S. patent application Ser. No. 61/220,417, entitled "High Voltage Pulse Assisted Aggregation and Separation of Algae," filed Jun. 25, 2009, the entirety of which is incorporated herein by reference.

FIELD OF THE INVENTION

The present invention relates to high voltage pulse assisted aggregation and separation of algae for dewatering and harvesting of algae.

BACKGROUND OF THE INVENTION

There is an increasing desire to develop sustainable fuel options that are not reliant of fossil fuels. One option being evaluated is the production of biofuels obtained from algae. The commercialization of such biofuels will likely require cultivating algae in large ponds. The ponds of algae would then be harvested and the lipids within the algae extracted and converted into biofuel. Existing methods of harvesting the algae have not proven commercially viable for numerous reasons, which include, but are not limited to: (i) too much water remains in the extracted algae for efficient lipid extraction, (ii) the algae cell walls are ruptured prematurely causing release of the valuable lipids before the extraction and conversion processes, and (iii) the algae cell walls are ruptured preventing the algae from being reused. Thus, there is a need for improvements related to the harvesting and processing of algae for the production of biofuels.

SUMMARY OF THE INVENTION

In one embodiment, a method of aggregating algae in a solution is disclosed. The method can include providing an algae feed comprising a liquid, e.g., water, and algae dispersed therein. The algae feed can then be aggregated by applying a nanosecond pulsed electric field to the algae feed.

The nanosecond pulsed electric field can be generated by a plurality of electric pulses having a pulse duration ranging from 1 to 1,000 nanoseconds. The peak electric field of the pulses can range from 1 to 1000 kV/cm. The peak power of the pulses can be at least 1 megawatt and the peak voltage of the pulses can range from 1 kV and 500 kV. The nanosecond pulsed electric field can be of an intensity and duration that the nanosecond pulsed electric field does not produce a plasma discharge or an arc discharge.

The method can include separating an aggregated algae stream from the algae feed. The aggregating step and the separating step can be performed continuously. The method can also include processing the aggregated algae stream to produce an algae-based biofuel.

The nanosecond pulsed electric fields can be applied for a duration sufficient to neutralize repulsive charges of the algae. The aggregating step can include adding one or more aggregating agents. The aggregating step can cause the algae in the feed stream to lose less than 10 wt-% of the lipid content of the algae.

Also disclosed is a system for aggregating algae. The system can include an aggregation reactor having at least one electrode. The at least one electrode can be in electrical communication with a power supply for applying nanosecond electric pulses to the electrodes. The electrodes can be in liquid communication with an algae feed contained in the aggregation reactor. The aggregation reactor can be in fluid communication with a separating reactor, which can be in fluid communication with a lipid extraction operation.

These and other embodiments are described in more detail below.

BRIEF DESCRIPTION OF THE DRAWINGS

A fuller understanding of the present invention and the features and benefits thereof will be obtained upon review of the following detailed description together with the accompanying drawings, in which:

FIG. 1 is a schematic of a system for high-voltage pulse assisted aggregation of algae (not to scale).

DETAILED DESCRIPTION

The invention is drawn to a method and device for harvesting algae suspended in a liquid feed stream. It has been unexpectedly discovered that when nanosecond electric pulses are applied to a solution containing algae, the algae aggregate without the need for the addition of an aggregation agent. While not wishing to be bound by theory and while not necessary for practicing the invention, it is believed that the nanosecond pulsed electric fields produce nanopores which allow transport of ions, such as sodium, potassium and calcium, across the algae cell membrane thereby neutralizing the repulsion between individual alga. However, the nanopores produced by the nanosecond electric pulses are not large enough to allow lipids found in the algae to be released. Nanosecond pulsed electric fields of high field strength may also change membrane morphology and in particular dipole alignments in the membrane. In addition, nanosecond pulsed electric fields may change surface charge layers and the distribution of free and bound charges in the matrix in general.

The method of harvesting algae can include providing an algae feed that includes algae dispersed in a liquid, e.g., water, brackish water, saline water or brine. The algae feed can be aggregated in a step that includes applying a nanosecond pulsed electric field to the algae feed. The nanosecond pulsed electric field can be produced by delivering a plurality of electric pulses having a pulse duration ranging from 1 nanosecond to 100,000 nanoseconds, 1 to 1,000 nanoseconds, or even 1 to 500 nanoseconds or even 10-300 nanoseconds to the electrodes. The duration of the electric pulses can be selected such that the algae aggregate while the cell walls of the algae do not lose their integrity.

The strength of the electric fields applied to the algae feed can depend on the pulse duration and can be selected so that they remain below the dielectric strength of water for a given pulse duration. Under these conditions, no breakdown (i.e., discharge between the high voltage electrode and the ground electrode) will occur. This is beneficial because such breakdowns have the potential to disrupt internal and outer cell membranes of the algae. The electric fields to which the algae feed is exposed can range from 0.1 to 100,000 kV/cm or from 10-1000 kV/cm.

The method can also include separating an aggregated algae stream from the algae feed after the nsPEFs have been applied. Depending of the pulsed exposure conditions, the aggregated algae may float to the top of the harvest tank, sink to the bottom of the harvest tank, or remain suspended in the harvest tank. Depending on the relative location of the aggregated algae, the aggregated algae can be harvested using an appropriate technology. Exposure conditions can also be varied to control the aggregation time, which can be as short as second, e.g., 1-60 seconds, or can take minutes, e.g., 1-60 minutes.

The aggregating step and separating step can occur as part of continuous flow reactor(s). In some embodiments, no aggregating agents are added during the aggregating step. The method can also include processing the aggregated algae stream to produce an algae biofuel. As used herein, the term "algae biofuel" is used to refer to algae-based fuels that include, but are not limited to, vegetable oil, biodiesel, bioethanol, biogasoline, biomethanol, biobutanol and other biofuels.

As used herein, the terms "aggregate" and "aggregation" are used to refer to a process where particles, e.g., algae, of a dispersion agglomerate or coagulate into larger groups of particles. As used herein, the term "aggregating agent" is used to refer to additives, such as salts, that facilitate aggregation of particles in dispersion. Exemplary aggregating agents include, but are not limited to, alum, aluminum chlorohydrate, aluminum sulfate, calcium oxidecalcium hydroxide, iron (III) chloride, iron (II) sulfate, polyacrylamide, polyDADMAC, sodium aluminate, sodium silicate, chitosan, *Moringa oleifera* seeds, papain, strychnos seeds, isinglass, and combinations thereof.

The nanosecond pulsed electric field can neutralize repulsive charges of the algae. In some embodiments, the nanosecond pulsed electric field does not produce a plasma discharge or arc discharge.

An unexpected benefit of the claimed method and device is that the algae do not undergo electroporation, which could cause premature release of lipids from the algae. As used herein, "electroporation" refers to a process where the cell membrane is temporarily made permeable enough to allow large molecules, such as propidium iodide or lipids, to cross the cell membrane. The algae can lose less than 10 wt-% of the lipid content of the algae as a result of the aggregating step, less than 5 wt-% of the lipid content of the algae as a result of the aggregating step, or less than 1 wt-% of the lipid content the algae as a result of the aggregating step, or even less than 0.5 wt-% of the lipid content the algae as a result of the aggregating step.

The peak electric field delivered to the algae feed by the pulses ranges from 0.1-100,000 kV/cm, or from 10 to 1,000 kV/cm, or from 50 to 500 kV/cm, or from 100 to 400 kV/cm. The peak power of the pulses can be at least 500 kW, or at least 1 megawatt. The peak voltage of the pulses can range from 1 kV and 500 kV, or from 10 kV to 450 kV, or from 50 kV to 300 kV.

It should be noted that while the delivery power is extremely high, the energy that is delivered can remain low due to the minimal pulse duration. The energy delivered with a single pulse can range from 0.1 to 100 joules, or 1 to 10 joules.

There are several additional unexpected advantages of the methods and devices disclosed herein. First, the method eliminates the need to use an agglomerating agent, which can provide a substantial cost savings. Second, the nanosecond pulses do not produce excess free charges in the algae feed, which limits galvanic processes that can lead to corrosion and eliminates the need for a sacrificial anode or other similar devices. Finally, the nanosecond pulses disclosed herein use substantially less energy than the continuous electrical energy required for electro-flocculation.

The invention also includes a system for harvesting algae. In the exemplary system shown in FIG. 1, the system 10 can include an algae reservoir 12 or other source. The algae reservoir 12 can include an algae feed 13, which can be an aqueous suspension containing algae 14. In the algae reservoir 12, the algae will generally be separated by the naturally-occurring repulsive forces of the algae 14.

An aggregation reactor 16 can be in fluid communication with the algae reservoir 12. The aggregation reactor 16 can include a nanosecond pulsed electric field (nsPEF) system 18. The nsPEF system 18 can include at least one electrode 20 and 22. The at least one electrode can include a working electrode 20 and a ground electrode 22. As shown in FIG. 1, the ground electrode 22 can be a cylindrical electrode that is concentrically arranged with a pipe of the aggregation reactor 16.

The at least one electrode 20, 22 can be in electrical communication with a power supply 24. At least one of the at least one electrodes 20, 22 can be in liquid communication with an algae feed 13 within the aggregation reactor 16. The power supply 24 can be designed for applying nanosecond electric pulses to the at least one electrode 20, 22. In alternative embodiments, the arrangement of the working and ground electrodes can be reversed.

The nanosecond electric pulses can have a pulse duration ranging from 1 to 1,000 nanoseconds. The pulse duration of the nanosecond electric pulses can be less than 500 nanoseconds, or less than 250 nanoseconds, or less than 100 nanoseconds, or less than 10 nanoseconds, or less than 1 nanosecond. The pulse duration of the nanosecond electric pulses can be at least 1 nanosecond, or at least 5 nanoseconds, or at least 10 nanoseconds. The pulse duration can range from any combination of the above minimum and maximum pulse durations, e.g., from 5 nanoseconds to 100 nanoseconds.

The system 10 can also include a separator 28 for separating aggregated algae 30 that have been treated by the aggregation reactor 16. The separator 28 can be part of the aggregation reactor 16. Alternatively, as shown in FIG. 1, the separator 28 can be separate from, but in fluid communication with, the aggregation reactor 16. For example, the aggregation reactor 16 can be a cylindrical reactor, e.g., a pipe reactor, connected to the separator 28 and the aggregated algae 30 can be separated from the aggregator effluent 32 using a raking technique.

The system 10 can also include a lipid extraction operation 34 in fluid communication with and down-stream from the aggregation reactor 16. The separator 28 can be in fluid communication with the lipid extraction operation 34. An aggregated algae stream 36 can exit the separator 28 and the aggregated algae stream 36 can be fed to the extraction operation 34 via a pipe 38.

The nanosecond electric pulses of the aggregation reactor 16 can be applied such that algae 14 in the algae feed 13 supplied to the aggregation reactor 16 lose less than 10 wt-% of a lipid content of the algae 14 as a result of the nanosecond electric pulses. The low lipid loss during the aggregation stage, simplifies the process by retaining the lipids in the algae until the algae are harvested and concentrated for lipid extraction. This enables higher efficiency harvesting of algae and results in higher efficiency production of algae biofuels.

It is to be understood that while the invention in has been described in conjunction with the preferred specific embodiments thereof and that the foregoing description is intended to illustrate and not limit the scope of the invention. Other aspects, advantages and modifications within the scope of the invention will be apparent to those skilled in the art to which the invention pertains.

We claim:

1. A method of aggregating algae in a solution, comprising: providing an algae feed comprising a liquid and algae dispersed therein, aggregating said algae feed, said aggregating comprising:
applying a nanosecond pulsed electric field to said algae feed, said nanosecond pulsed electric field generated by a plurality of electric pulses having a pulse duration ranging from 1 to 500 nanoseconds, wherein the nanosecond pulsed electric field neutralizes repulsive charges of said algae.

2. The method according to claim 1, further comprising: separating an aggregated algae stream from said algae feed after the applying step.

3. The method according to claim 2, wherein the aggregating step and the separating step are performed continuously.

4. The method according to claim 2, further comprising: processing said aggregated algae stream to produce an algae biofuel.

5. The method according to claim 1, wherein said algae lose less than 10 wt-% of a lipid content of said algae as a result of said aggregating step.

6. The method according to claim 1, wherein said nanosecond pulsed electric field produces neither a plasma discharge nor an arc discharge.

7. The method according to claim 1, wherein a peak electric field produced in said algae feed by said pulses ranges from 1 to 1000 kV/cm.

8. The method according to claim 1, wherein a peak power of said electrical pulses is at least 1 megawatt.

9. The method according to claim 1, wherein a peak voltage of said electrical pulses ranges from 1 kV to 500 kV.

10. The method according to claim 1, wherein the aggregating step comprises adding aggregating agents.

* * * * *